US00PP36593P2

(12) United States Plant Patent
Petersen

(10) Patent No.: US PP36,593 P2
(45) Date of Patent: Apr. 8, 2025

(54) ***SESLERIA* PLANT NAMED 'OVER2021'**

(50) Latin Name: *Sesleria heufleriana*
Varietal Denomination: OVER2021

(71) Applicant: A-Plant 2000 ApS, Gislev (DK)

(72) Inventor: Poul Petersen, Hoersholm (DK)

(73) Assignee: A-PLANT 2000 APS, Gislev (DK)

( * ) Notice: Subject to any disclaimer, the term of this patent is extended or adjusted under 35 U.S.C. 154(b) by 0 days.

(21) Appl. No.: 18/900,765

(22) Filed: Sep. 29, 2024

Related U.S. Application Data

(60) Provisional application No. 63/601,936, filed on Nov. 22, 2023.

(51) Int. Cl.
*A01H 5/02* (2018.01)
*A01H 6/00* (2018.01)

(52) U.S. Cl.
USPC ..... Plt./384
CPC ..... *A01H 6/00* (2018.05)

(58) Field of Classification Search
USPC ..... Plt./384
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Sesleria* plant named 'OVER2021' that is characterized by its broad leaves, its leaves with an upper surface that is bluish in color, and its flower spikes that are blue-black in color.

4 Drawing Sheets

Botanical classification: *Sesleria heufleriana.*
Cultivar designation: 'OVER2021'.

BACKGROUND OF THE INVENTION

The present invention relates to a new and distinct cultivar of *Sesleria heufleriana* and will be referred to hereafter by its cultivar name, 'OVER2021'. 'OVER2021' represents a new cultivar of cold hardy, perennial ornamental grass grown for landscape use.

'OVER2021' was discovered by the Inventor as a seedling from amongst over 1000 seedlings of unpatented and unnamed plants of *Sesleria heufleriana* that were growing in a trial field in Hoersholm, Denmark in summer of 2017. The parentage is unknown.

Asexual propagation of the new cultivar was first accomplished by division by the Inventor in 2017 in Hoersholm, Denmark. Asexual propagation by division has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'OVER2021' as a unique cultivar of *Sesleria.*

1. 'OVER2021' exhibits broad leaves.
2. 'OVER2021' exhibits leaves with an upper surface that is bluish in color.
3. 'OVER2021' exhibits flower spikes that are blue-black in color.

'OVER2021' can be most closely compared to typical plants of the species *Sesleria heufleriana* and *Sesleria caerulea* and *Sesleria* 'Greenlee Hybrid' (not patented). Typical plants of *Sesleria heufleriana* are similar to 'OVER2021' in having similar flowers and bluish tinted foliage but differ from 'OVER2021' in having a less vigorous plant habit and a more rounded plant habit. Typical plants of *Sesleria caerulea* differ from 'OVER2021' in having a shorter plant height, leaves that are not as broad and less blue in color, and a slower growing habit. 'Greenlee Hybrid' is similar in having a bluish cast in the upper surface of the leaves. 'Greenlee Hybrid' differs from 'OVER2021' in having less broad foliage, a shorter plant height and a denser plant habit.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Nordic Plants, Hennecke Stauder, Gug Planteskole, Cramers Blommor, Haveselskabet, Kolonilotten, Gunnebo Tradgard, Skraedderbakkens Havecenter (facebook), Jespers Planteskole, Moesgaard Have Center, Overdam Planteskole, and Gunnar Christensens Planteskole.

BRIEF DESCRIPTION OF THE DRAWINGS

The accompanying color photographs illustrate the overall appearance and distinct characteristics of the new *Sesleria*. The photographs In FIG. 1, FIG. 2, and FIG. 3 were taken of a plant 2-years-in-age as field grown in Boskoop, The Netherlands.

The photograph in FIG. 1. provides a top view of a plant of 'OVER2021' and illustrates the plant habit.

Figure 1:
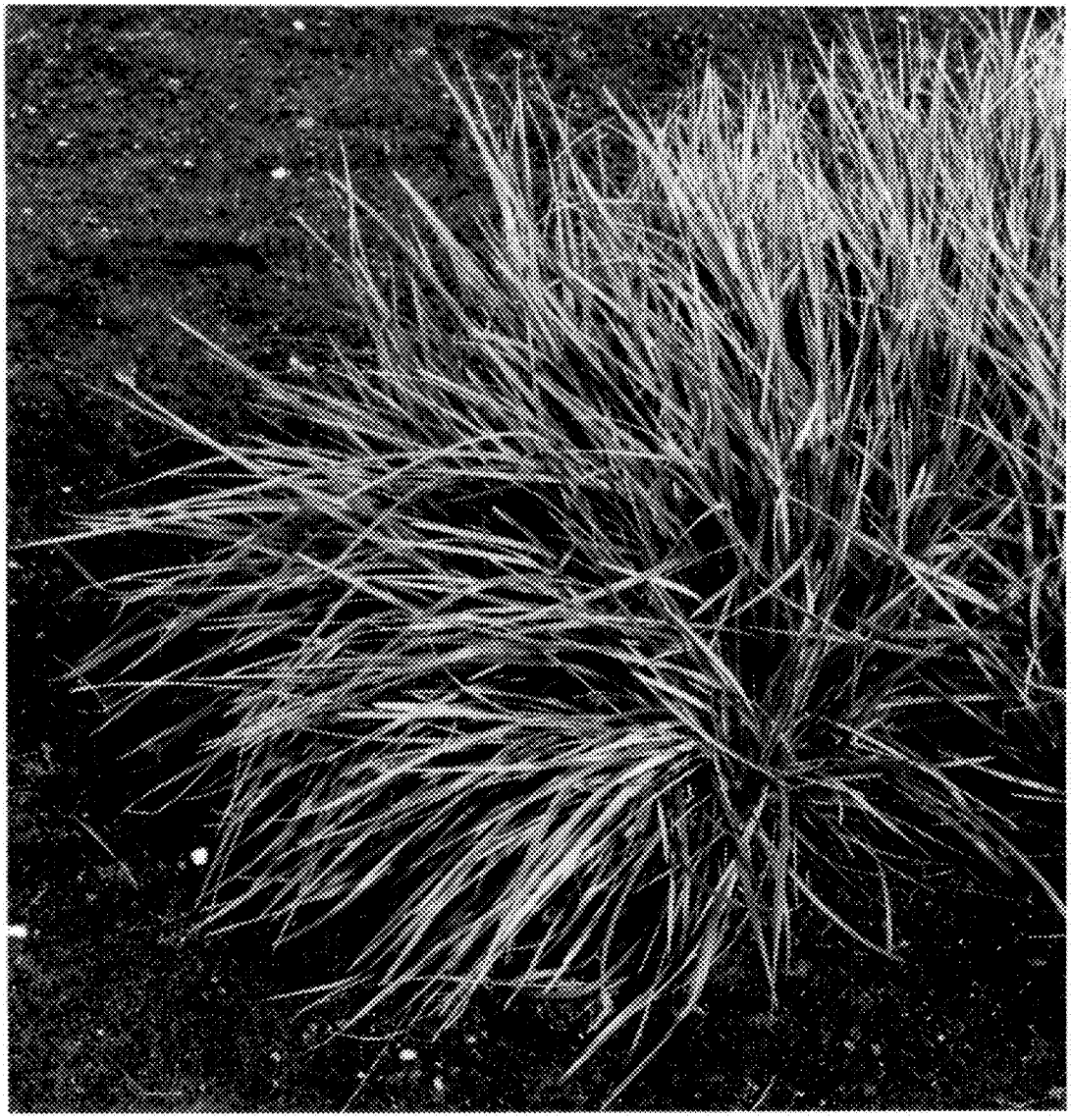
Figure 2:
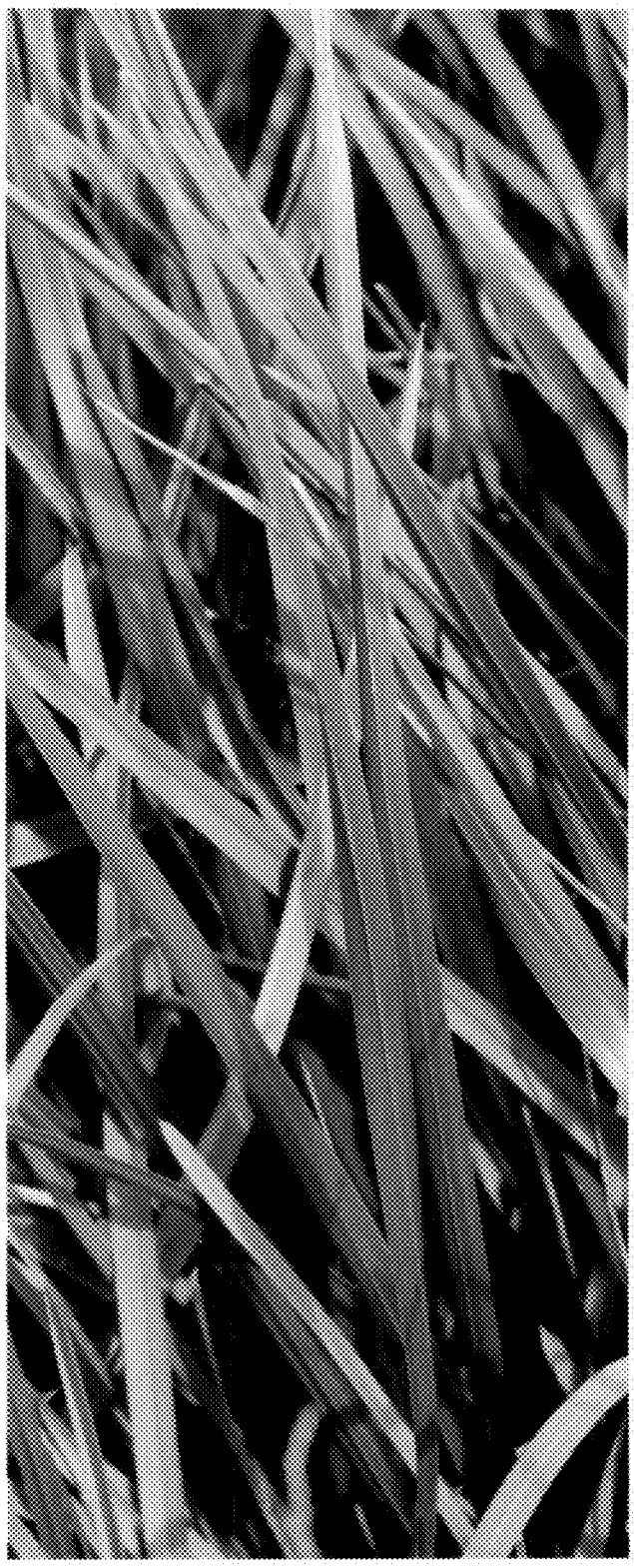

The photograph in FIG. 2. provides a close-up view of the lower surface of the foliage of 'OVER2021'.

Figure 3:
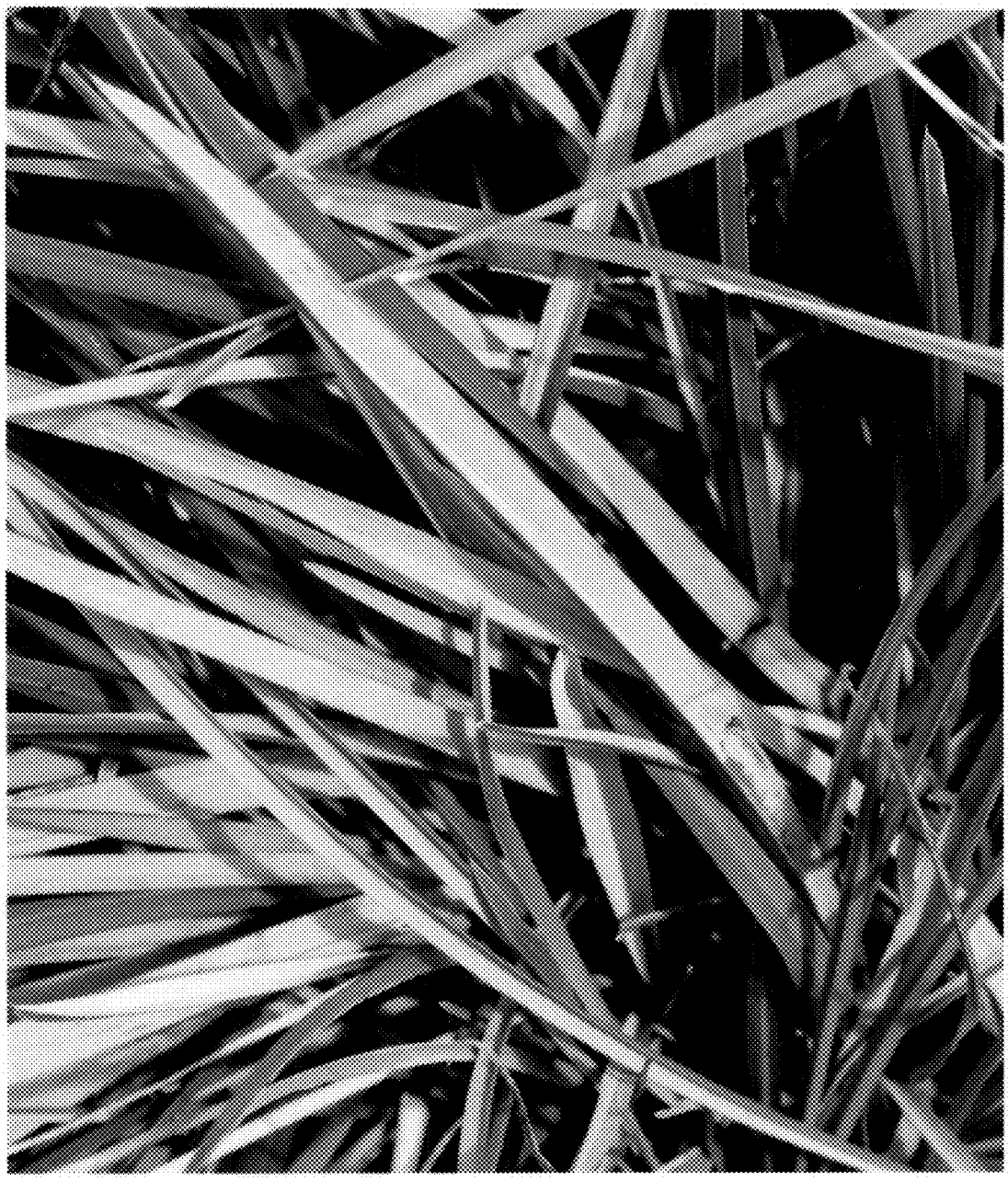

The photograph in FIG. 3. provides a close-up view of the upper surface of the foliage of 'OVER2021'.

Figure 4:
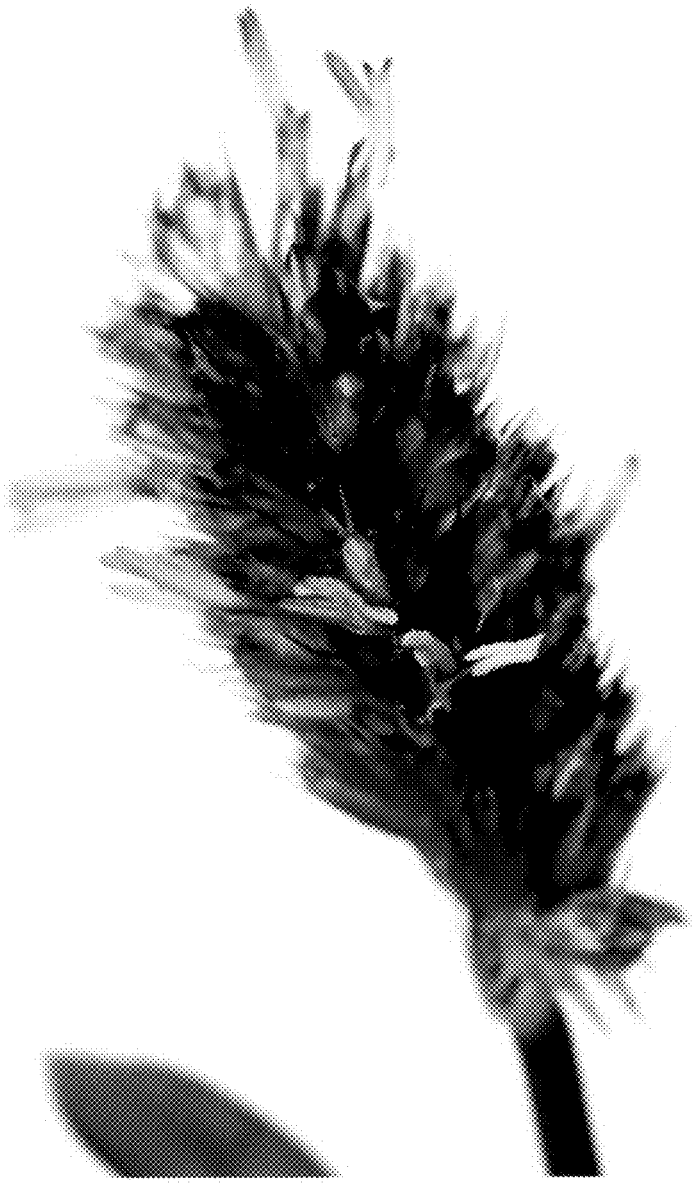

The photograph in FIG. 4. was taken of a plant 2 years in age as field grown in Boskoop, The Netherlands and provides a close-up view of an inflorescence of 'OVER2021'.

The colors in the photographs are as close as possible with the photographic and printing technology utilized and the color values cited in the Detailed Botanical Description accurately describe the colors of the new *Sesleria*.

DETAILED BOTANICAL DESCRIPTION

The following is a detailed description of 2-year-old plants of the new cultivar as field grown in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Blooms early March to late April in Denmark.

*Plant type*.—Herbaceous perennial grass.

*Plant habit*.—Clump-forming, compact, upright with cascading foliage.

*Plant shape*.—Broadly obovate to broadly inverted triangular.

*Height and spread*.—Average of 65 cm in height and 76 cm in spread as a 2-year-old field grown plant.

*Cold hardiness*.—At least in U.S.D.A. Zones 4.

*Diseases and pests*.—No susceptibility or resistance to diseases or pests has been observed.

*Root description*.—Thin, fleshy, no stolons or rhizomes present.

*Root development*.—An average of 3 weeks for root development, average of 2 months to produce a young rooted plant.

*Propagation*.—Division.

*Growth rate*.—Moderate.

*Branching*.—No branches present, average of 86 basal shoots.

Foliage description:

*Leaf shape*.—Linear.

*Leaf division*.—Simple.

*Leaf base*.—Broadly cuneate, sheathed, sheath; 9.3 cm in length and width, color; 160D, base 144B.

*Leaf apex*.—Acute, with a soft mucronate tip.

*Leaf aspect*.—Strongly carinate.

*Leaf venation*.—Parallel, only main vein is visible, upper side 188B, lower side 147C.

*Leaf margins*.—Entire, slightly sharp, serrate-dentate, no undulation.

*Leaf size*.—48.2 cm in length, 8.5 mm in width.

*Leaf (blade and sheath) surface*.—Both surfaces glabrous and smooth, upper surface matte, lower surface slightly to moderately glossy.

*Leaf number*.—An average of 5 per culm.

*Leaf arrangement*.—Equitant.

*Leaf color*.—Young upper surface; 143B, covered with a very thin waxy layer 191B, young lower surface; a blend of 141B and 143A, mature upper surface NN137C, covered with a waxy layer a blend of 189A and 189B, mature lower surface; a blend of NN137A and 147A.

Flower description:

*General description*.—Compact, spike-like panicle.

*Lastingness of inflorescence*.—Average of 1 month for spikelets to drop, rest of raceme persistent into winter.

*Fragrance*.—None.

*Panicle size*.—Average of 3.1 cm in length and 1.8 cm in diameter.

*Flower number*.—An average of 200 flowers per inflorescence, 4,300 flowers per plant.

*Flower buds*.—An average of 7 mm in length, 2 mm in diameter, ovate in shape, color; 143C, tinged with a blend of N186B and 203C, surface is slightly glossy and densely covered with silky adpressed hairs, too small to measure size or color.

*Peduncle (rachis)*.—13.8 cm in length, 1 mm in width, moderately strong, held in an angle of 75° to soil level, surface smooth and slightly glossy and 139A in color.

*Pedicels*.—None present.

*Spikelet description (flowers)*.—Single, flowers consisting of 2 glumes, 1 lemma and 1 palea, 2 glumes oppositely placed at the base of each individual flower, lemma and palea oppositely, alternately placed above the glumes, glumes, lemma and palea glabrous, very slightly glossy, ovate in shape, strongly concave, margins entire and densely covered with very short adpressed silky hairs, color is too small to measure, bases of glumes, lemma and palea cuneate, apices of glumes and lemma narrow aristate (awn-like), apex of palea emarginate, average length of glumes 8 mm, average length of palea 5 mm, average length lemma 5 mm, average width of glumes 3 mm, average width of lemma and palea 0.2 mm, color; when opening and at maturity, both sides of glumes, palea and lemma transparent and 145D, midrib of glumes and lemma and margins of palea darker 144A and 144B, top of palea N187A, no venation visible, glumes, palea and lemma not fading.

Reproductive organs:

*Androecium*.—Stamens; average of 3, anthers; narrow oblong and dorsifixed in shape, 4 mm in length, 0.75 mm in width, color; young a blend of 183A and 200B, mature a blend of 1B to 1C, filament; 6 mm in length, transparent and N155A in color, pollen; low and 1C in color.

*Gynoecium*.—Pistil; 1, 8 mm in length, stigmas; plumose, 0.4 mm in length, 0.3 mm in diameter, N155A in color, style; 0.4 mm in length, N155A in color, ovary; 144B in color.

It is claimed:

1. A new and distinct cultivar of *Sesleria* plant named 'OVER2021' as herein illustrated and described.

* * * * *